United States Patent
Katra et al.

(10) Patent No.: US 10,905,351 B2
(45) Date of Patent: Feb. 2, 2021

(54) MEDICAL DEVICE AND METHODS OF MONITORING A PATIENT WITH RENAL DYSFUNCTION

(71) Applicant: Medtronic Monitoring, Inc., San Jose, CA (US)

(72) Inventors: Rodolphe Katra, Blaine, MN (US); Niranjan Chakravarthy, Eden Prairie, MN (US); Imad Libbus, St. Paul, MN (US)

(73) Assignee: Medtronic Monitoring, Inc., San Jose, CA (US)

( * ) Notice: Subject to any disclaimer, the term of this patent is extended or adjusted under 35 U.S.C. 154(b) by 504 days.

(21) Appl. No.: 15/386,296

(22) Filed: Dec. 21, 2016

(65) Prior Publication Data

US 2017/0100053 A1    Apr. 13, 2017

Related U.S. Application Data

(62) Division of application No. 12/878,873, filed on Sep. 9, 2010, now Pat. No. 9,554,725.
(Continued)

(51) Int. Cl.
*A61B 5/053* (2006.01)
*A61B 5/0537* (2021.01)
(Continued)

(52) U.S. Cl.
CPC .......... *A61B 5/0537* (2013.01); *A61B 5/0538* (2013.01); *A61B 5/4836* (2013.01);
(Continued)

(58) Field of Classification Search
CPC ....... A61B 5/0537; A61B 5/4836; A61M 1/14
See application file for complete search history.

(56) References Cited

U.S. PATENT DOCUMENTS 4,008,712 A * 2/1977 Nyboer ............... A61B 5/0537
600/547
5,902,336 A 5/1999 Mishkin
(Continued)

FOREIGN PATENT DOCUMENTS

| WO | WO-2009/036313 | 3/2009 |
| WO | WO-2009/036321 | 3/2009 |

(Continued)

OTHER PUBLICATIONS

Yamamoto, et al., Instantaneous Measurement of Electrical Parameters in a Palm During Electrodermal Activity, Apr. 1996, IEEE Transactions on Instrumentation and Measurement, vol. 45, No. 2, p. 483-487. (Year: 1996).*

(Continued)

*Primary Examiner* — Daniel L Cerioni
*Assistant Examiner* — Raymond P Dulman
(74) *Attorney, Agent, or Firm* — Shumaker & Sieffert, P.A.

(57) ABSTRACT

Embodiments relate to a method of monitoring physiological parameters of a patient with renal dysfunction. The method includes electrically connecting one or more medical device electrodes with a measurement site of a patient, generating one or more first stimulation signals sufficient to provide input physiological parameters specific to the patient, measuring one or more first bioimpedance values from the generated signals, analyzing at least one of the input physiological parameters within the one or more first bioimpedance values and generating a personalized dialysis program. The systems and methods can further provide essentially real-time data of patient undergoing treatment and control of treatment to a patient.

12 Claims, 8 Drawing Sheets

Related U.S. Application Data

(60) Provisional application No. 61/370,345, filed on Aug. 3, 2010.

(51) Int. Cl.
*A61B 5/0538* (2021.01)
*A61B 5/00* (2006.01)
*A61M 1/14* (2006.01)
*A61B 5/021* (2006.01)
*A61B 5/0295* (2006.01)

(52) U.S. Cl.
CPC ............... *A61M 1/14* (2013.01); *A61B 5/021* (2013.01); *A61B 5/0295* (2013.01)

(56) References Cited

U.S. PATENT DOCUMENTS

| | | |
|---|---|---|
| 6,512,949 B1 | 1/2003 | Combs et al. |
| 6,615,077 B1 * | 9/2003 | Zhu .................. A61B 5/022 600/547 |
| 7,177,681 B2 | 2/2007 | Zhu et al. |
| 7,400,920 B1 | 7/2008 | Gill et al. |
| 7,647,101 B2 | 1/2010 | Libbus et al. |
| 7,758,562 B2 | 7/2010 | Gelfand et al. |
| 8,831,717 B2 * | 9/2014 | Solem .................. A61B 5/0535 600/300 |
| 9,554,725 B2 | 1/2017 | Katra et al. |
| 2004/0147871 A1 | 7/2004 | Burnett |
| 2005/0288730 A1 | 12/2005 | Deem et al. |
| 2006/0235353 A1 | 10/2006 | Gelfand et al. |
| 2006/0253064 A1 | 11/2006 | Gelfand et al. |
| 2006/0270971 A1 | 11/2006 | Gelfand et al. |
| 2006/0287585 A1 | 12/2006 | Hamada et al. |
| 2007/0055198 A1 | 3/2007 | O'Mahony |
| 2007/0060874 A1 | 3/2007 | Nesbitt et al. |
| 2007/0175827 A1 | 8/2007 | Wariar |
| 2008/0071147 A1 * | 3/2008 | Chamney .............. A61B 5/537 600/300 |
| 2008/0140000 A1 | 6/2008 | Shuros et al. |
| 2008/0255642 A1 | 10/2008 | Zarins |
| 2009/0043222 A1 * | 2/2009 | Chetham .............. A61B 5/0537 600/547 |
| 2009/0062730 A1 | 3/2009 | Woo |
| 2009/0099475 A1 | 4/2009 | Bjorling |
| 2009/0275808 A1 | 11/2009 | DiMaio |
| 2010/0063438 A1 * | 3/2010 | Bengtsson ........ A61M 5/14248 604/66 |
| 2010/0099964 A1 * | 4/2010 | O'Reilly ............ A61B 5/14551 600/323 |
| 2010/0185142 A1 | 7/2010 | Kamen et al. |
| 2011/0125049 A1 * | 5/2011 | Nabutovsky ........... A61B 5/021 600/547 |
| 2014/0031787 A1 | 1/2014 | Burnes et al. |
| 2014/0148656 A1 | 5/2014 | Zielinski et al. |

FOREIGN PATENT DOCUMENTS

| | | |
|---|---|---|
| WO | WO-2009/036327 | 3/2009 |
| WO | WO-2009/036329 | 3/2009 |
| WO | WO-2009/036369 | 3/2009 |

OTHER PUBLICATIONS

Kyle, et al., "Bioelectrical Impedance Analysis—part I: review of principles and methods", *Clin Nutr.*, vol. 23 (5) (Oct. 2004),pp. 1226-1243.

Yu, et al., "Intrathoracic Impedance Monitoring in Patients with Heart Failure: Correlation with Fluid Status and Feasibility of Early Warning Preceding Hospitalization", *Circulation*, vol. 112, (2005),pp. 841-848.

Cianci, "Body fluid compartments in hypertension", *European Review for Medical and Pharmacological Sciences*, vol. 10, (2006),pp. 75-78.

Prosecution History from U.S. Appl. No. 12/878,873, dated May 14, 2013 through Sep. 22, 2016, 117 pp.

\* cited by examiner

MEDICAL DEVICE AND METHODS OF MONITORING A PATIENT WITH RENAL DYSFUNCTION

The present application is a divisional of U.S. Non-Provisional patent application Ser. No. 12/878,873; titled MEDICAL DEVICE AND METHODS OF MONITORING A PATIENT WITH RENAL DYSFUNCTION; and filed on 9 Sep. 2010, which is related to and claims benefit of U.S. Provisional Patent Application No. 61/370,345; titled MEDICAL DEVICE AND METHODS OF MONITORING A PATIENT WITH RENAL DYSFUNCTION; and filed 3 Aug. 2010, which is hereby incorporated by reference for any purpose.

BACKGROUND

Dialysis is primarily used to provide an artificial replacement for lost kidney function in people with renal failure. Dialysis may be used for those with an acute disturbance in kidney function or for those with progressive but chronically worsening kidney function (i.e., chronic kidney disease). The kidneys have important roles in maintaining health. When healthy, the kidneys maintain the body's internal equilibrium of water and minerals (sodium, potassium, chloride, calcium, phosphorus, magnesium, sulfate, for example). Those acidic metabolism end products that the body cannot get rid of via respiration are also excreted through the kidneys.

Dialysis treatment is often performed multiple times a week and for a number of hours per session. This is currently done on a fixed calendar schedule or according to physician discretion. Such discretion may be driven by symptoms or laboratory results, which require repeat health care visits. Often, such procedures are associated with increased morbidity rates.

If monitoring a patient's physiological conditions outside of a hospital setting, the devices utilized are often painful or uncomfortable for a patient to use and with which take measurements. Such intrusive devices and methods may lead to poor patient compliance. It is often difficult or not practical for a doctor to monitor a patient's health status remotely or to have access to long term measurements of a number of physiological parameters. Additionally, temporal measurements monitored within a patient may be susceptible to chronically changing proportions of fat and fluid that may mask the underlying deterioration in patient health status.

SUMMARY

Embodiments relate to a method of monitoring physiological parameters of a patient with renal dysfunction. The method includes connecting one or more medical device electrodes with a measurement site of a patient, generating one or more stimulation signals sufficient to provide input physiological parameters specific to the patient, measuring one or more bioimpedance values from the generated signals, analyzing at least one of the input physiological parameters within the one or more first bioimpedance values and generating a personalized dialysis program.

Embodiments further describe a medical device, including a measuring interface located between a device and a measurement site of a patient, one or more electrodes to generate one or more stimulation signals positioned at the measuring interface and in electrical contact with the measurement site, circuitry to measure one or more bioimpedance values as a result of the generated stimulation signals from the one or more electrodes and a processor system to a identify one or more physiological parameters, including renal parameters, from the one or more bioimpedance values.

BRIEF DESCRIPTION OF THE DRAWINGS

The accompanying drawings illustrate non-limiting example embodiments of the invention.

DETAILED DESCRIPTION

Figure 2:
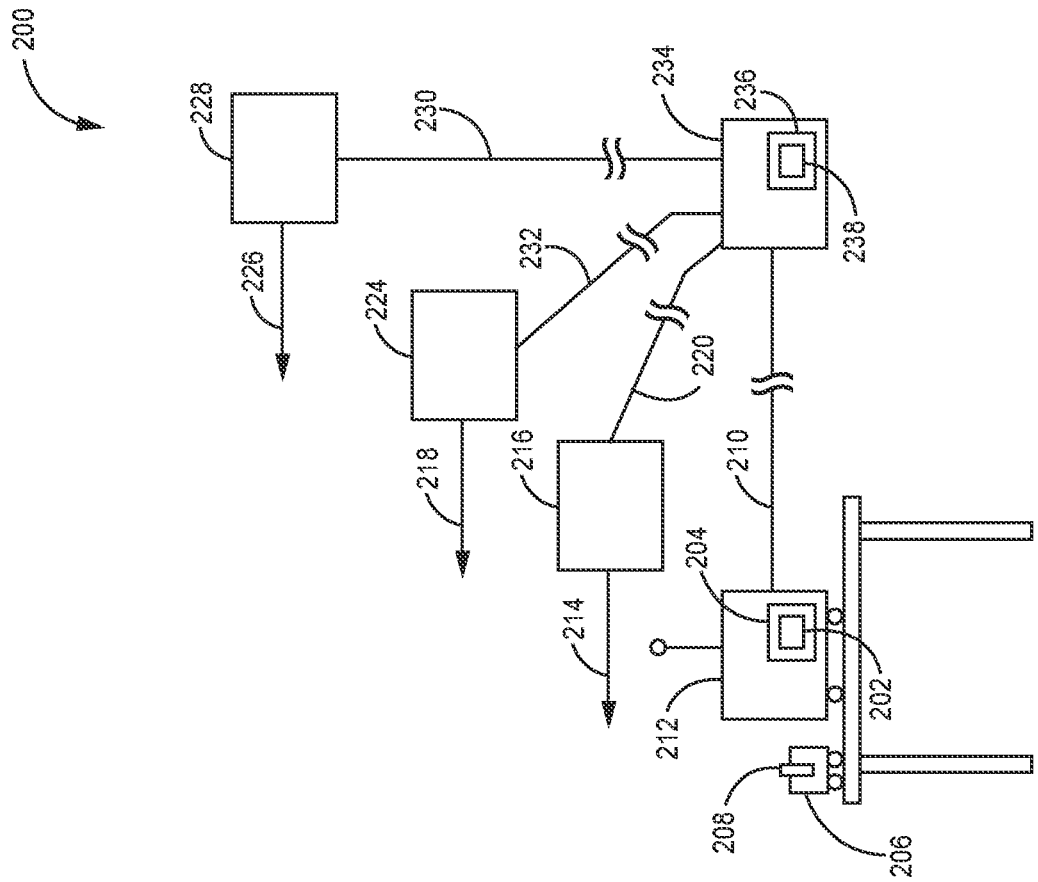
FIG. 2 illustrates a schematic view of monitoring and treatment system, according to some embodiments.

Throughout the following description, specific details are set forth in order to provide a more thorough understanding of the invention. However, the invention may be practiced without these particulars. In other instances, well known elements have not been shown or described in detail in order to avoid unnecessarily obscuring the invention. The drawings show, by way of illustration, specific embodiments in which the invention may be practiced. These embodiments may be combined, other elements may be utilized or structural or logical changes may be made without departing from the scope of the invention. Accordingly, the specification and drawings are to be regarded in an illustrative, rather than a restrictive, sense.

All publications, patents and patent documents referred to in this document are incorporated by reference herein in their entirety, as though individually incorporated by reference. In the event of inconsistent usages between this document and those documents so incorporated by reference, the usage in the incorporated references should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more". In this document, the term "or" is used to refer to a nonexclusive or, such that "A, B or C" includes "A only", "B only", "C only", "A and B", "B and C", "A and C", and "A, B and C", unless otherwise indicated. The terms "above" and "below" are used to describe two different directions in relation to the center of a composite and the terms "upper" and "lower" may be used to describe two different surfaces of a composite. However, these terms are used merely for ease of description and are not to be understood as fixing the orientation of the described embodiments. In the appended aspects or claims, the terms "first", "second" and "third", etc. are used merely as labels, and are not intended to impose numerical requirements on their objects.

Embodiments of the present invention relate to a bioimpedance medical device and methods for measuring physiological parameters using the same. Bioimpedance and other physiological parameters may be used to non-invasively monitor the need for dialysis in patients with kidney dysfunction. By using bioimpedance measurements personalized to a patient's specific characteristics and demographics, physicians may determine when and if dialysis is needed, the progression and time course of dialysis therapy and remotely monitor the patient's changes in fluid retention, electrolyte imbalance and hydration level, for example. Bioimpedance may be used as replacement for measuring fluid removal during dialysis and as a more sensitive and specific metric than weight change. Additionally, measurements may be taken while the patient is away from the hospital or clinic for providing long-term tracking of physiological conditions. The embodiments may be used for a single or one-time analysis of a patient for screening or undergoing dialysis treatment or alternatively, may be used to track a patient's change in physiological conditions over time—both while in a health care facility and while at home. Embodiments describe a method and algorithm that utilizes specific and unique parameters to generate and implement a patient specific and personalized dialysis management program and report. The system may establish ranges of normal and abnormal physiological parameters that are unique to each patient and relative to the patient's specific characteristics.

Figure 1:
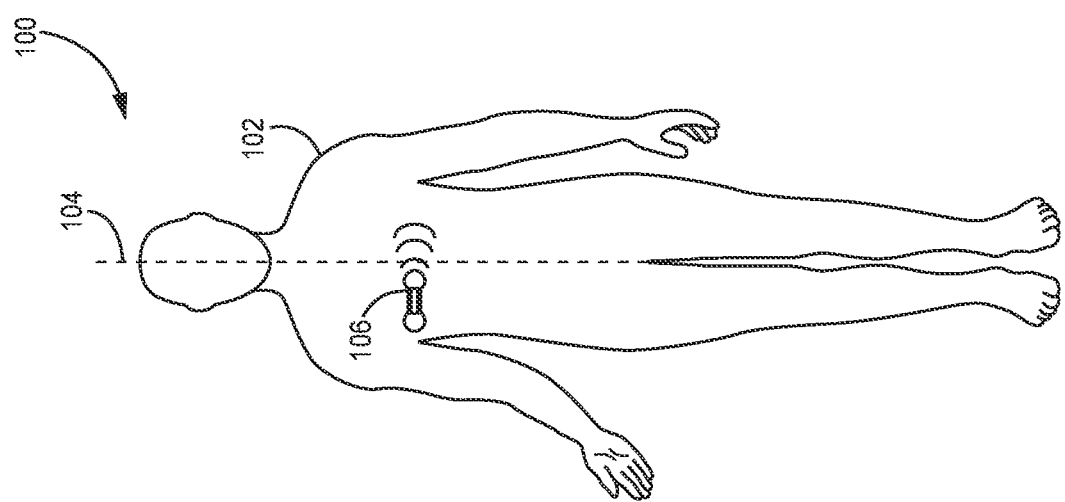
FIG. 1 illustrates a schematic view of a patient utilizing a medical device measuring one or more bioimpedance values, according to some embodiments.

Referring to FIG. 1, a schematic view 100 of a patient utilizing a medical device measuring one or more bioimpedance values is shown, according to some embodiments. A patient 102 may utilize a medical device 106 on either side a midline 104. The device may also be used medially from the midline such as in the periphery of a patient's body as well, e.g., hands or feet. The medical device 106 can be an adherent device on the surface of the skin. The medical device 106 can be an implantable medical device. If implantable, the device may be integrated with medical devices performing other tasks or functions, such as a pacemaker or cardiac defibrillator, for example. An example of an implantable device that can be adapted to perform embodiments of the present invention includes U.S. Pat. Nos. 7,400,920 and 7,177,681. The medical device 106 may be partially implantable in one embodiment. The device 106 can further be part of an external medical device such as an insulin pump. The device 106 may be positioned on or in the patient in many possible positions, so long as one or more electrodes of the device are in electrical contact or connectivity with a portion (i.e., measurement site) of the patient's body capable of providing one or more bioimpedance values when stimulated. Examples of such portions, include skin, tissue, interstitial fluid or blood, among others. Measurement sites may be chosen to minimize interferent signal and maximize the desired component signals. For example, if fat is an interferent, a portion of the body with less fat and more muscle present may be chosen as the measurement site. The device 106 may be part of a hospital or clinic instrument utilized during dialysis, for example. The device 106 can include sensors that sense at least one of several physiological parameters, including electrical cardiac activity, heart rate, heart rate variability, autonomic balance, respiration, patient activity, temperature, and thoracic fluid.

Referring to FIG. 2, a schematic view 200 of monitoring and treatment system is shown, according to some embodiments. The device 106 of FIG. 1 may communicate with a remote center 234, located remotely from the device 106. The remote center 234 can be located within the same room or thousands of miles away from the device 106. The device 106 can communicate wirelessly with an intermediate device 212, such as through the internet or cellular phone system. The intermediate device 212 can communicate directly with the medical device 106 and then relay information to the remote center 234, for example. The medical device 106 and monitoring system can include a distributed processing system, for example. The distributed processing system can include at least one processor located on-board the medical device 106, at least one processor 204 on the intermediate device 212 and at least one processor 236 on the remote center 234, each of which processors is in electronic communication with the other processors. The processor 204 includes a tangible medium 202 and logic circuits to execute instructions in the tangible medium. The processor 236 includes a tangible medium 238 and logic circuits to execute instructions in the tangible medium. Remote processor 236 may include a backend server located at the remote center 234. Remote center 234 may be in communication with a health care provider 216 with a communication system 220, such as the internet, phone lines, wireless and/or satellite phone, for example. Health care provider 216, such as a family member, may be in communication with the patient 102, for example with a two way communication system 214, such as by cellular phone, email or landline phone.

Remote center 234 can be in communication with a health care professional 224, such as a physician, through a communication system 232. System 232 is an electrical or optical communication system, and may include the internet, an intranet, phone lines, wireless devices and/or satellite phone. Health care professional 224 may be in communication with patient 102 with two-way communication system 218. Remote center 234 may be in communication with an emergency responder 228, such as an operator or paramedic for example, with communications system 230. Responder 228 may travel 226 to the patient 102. Thus, in many embodiments, the monitoring and treatment systems associated with device 106 may form a close communication loop in response to signals from the device 106.

In many embodiments, the device 106 includes a reusable or rechargeable electronics module. One module 208 may be recharged using a charging station 206 while another module is located within the device. In some embodiments, the intermediate device 212 can include a charging module, data transfer, storage and/or transmission, such that one of the electronics modules can be placed in the intermediate device for charging and/or data transfer while the other electronics module is worn by the patient.

Figure 3:
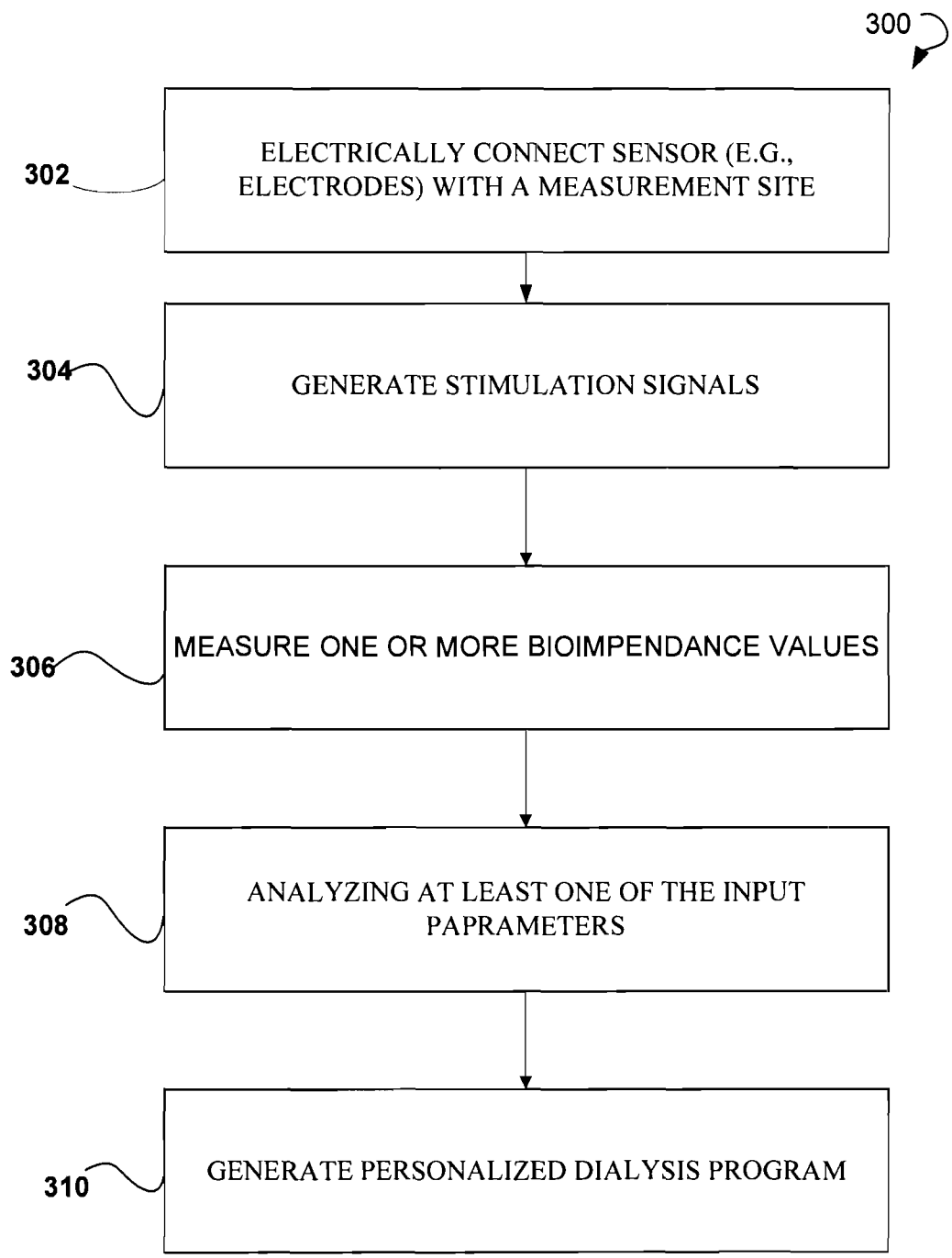
FIG. 3 illustrates a block flow diagram of a method of monitoring and analyzing physiological conditions within a patient, according to some embodiments.

Referring to FIG. 3, a block flow diagram 300 of a method of monitoring and analyzing a patient is shown, according to some embodiments. One or more electrodes can be electrically connected 302 with a measurement site of a patient. One or more stimulation signals can be generated 304 sufficient to provide input physiological parameters specific to the patient. One or more bioimpedance values (i.e., first bioimpedance values) may be measured 306 from the generated signals, for example. At least one of the input physiological parameters may be analyzed 308 within the one or more bioimpedance values. A personalized dialysis display or program may then be generated 310.

The one or more electrodes can be positioned on or in a medical device. The medical device may be an implant, a partial implant or an adherent device. In an example, an adherent device is removably attached to a patient's body. The bioimpedance medical device may be integrated with one or more other functional devices, such as pacemakers or glucose monitors, for example. The one or more electrodes can electrically connect 302, such as by contacting a portion of a patient that is capable to responding to a stimulation signal (i.e., measurement site). Electrically connect 302 refers to any contact between one or more electrodes and a portion of a patient's body such that an electrical signal can be generated or stimulated as well as sensed. The device may be independently utilized at a clinic during a dialysis treatment or integrated into other hospital equipment used during dialysis.

Examples of such adherent devices for use with the present disclosure can include the devices described in PCT publication WO 2009/036329; WO 2009/0363279; WO 2009/036321; and WO 2009/036313.

One or more stimulation signals can be generated 304. First signals can be generated in establishing baseline or input physiological data. Second or subsequent signals can be generated to monitor long-term care or spot check a patient's status. The device can generate multiple spot frequencies or a frequency sweep, for example. Spot frequency values can be chosen based on known bioimpedance reactions of certain biological components at a certain measurement site. For example, a signal may be generated at a frequency where electrolytes are known to resist an electrical current. In another example, a signal can be generated and applied to a patient at a frequency where fluid is known to interact with the signal. An example of a frequency sweep would be to generate signals at multiple values at set intervals. Signals generated 304 may be between about 5 kHz to about 1000 kHz, between about 100 kHz and about 800 kHz or between about 50 kHz and about 500 kHz, for example. Alternatively, signals generated 304 may be between about 0.5 kHz and about 5 kHz, about 3 kHz to about 10 kHz, between about 10 kHz and about 50 kHz or between about 20 kHz and about 75 kHz, for example. Types of waveforms may include sine, square, triangle, composite, sawtooth signals or a combination thereof. Other finer signals can be used as the signals provoking a signal response or signal change. An example of the applied signals can be 10 kHz, 100 kHz, and 1000 kHz, +/−10%. The signals sensed from this stimulation can be amplitude attenuated or frequency attenuated. It will be understood that the above recited frequencies are examples and other frequencies may prove to more accurate in assessing the condition of the patient. Generally, it is desired to apply a plurality of different frequencies in discrete steps and at discrete times to be able to sense the physiological parameters of the patient to measure renal function.

One or more bioimpedance values may be measured 306 from the generated signals, for example. Measuring 306 may include measuring resistance, reactance or changes in resistance and/or reactance over time, for example. Physiological parameters that may be measured include amounts of fat, fluid, ions, hydration levels, blood flow or combinations thereof, for example. Input physiological parameters may be used for establishing a baseline or initial conditions of a patient. This is especially useful in tracking long term health care status. Subsequent or second bioimpedance values may be measured for monitoring long term care or for spot checking a patient's health at that moment. The second or subsequent values may then be compared to the input parameters, thus creating an evaluation custom to that specific patient.

At least one of the input parameters may be analyzed 308 within the one or more bioimpedance values. Analyzing 308 may include identifying, isolating and quantifying individual or group physiological component values. Analyzing 308 may include subtracting measurement signals, combining measurements or isolating measurements for example. Analyzing 308 may include identifying correlations or lack of correlations between physiological component values. Analyzing 308 input parameters assists in establishing a patient's baseline or characteristic physiological conditions. Analysis of second or subsequent parameters provides long-term care information or allows for comparison of a patient's current health to data points in the past, for example.

Figure 7:
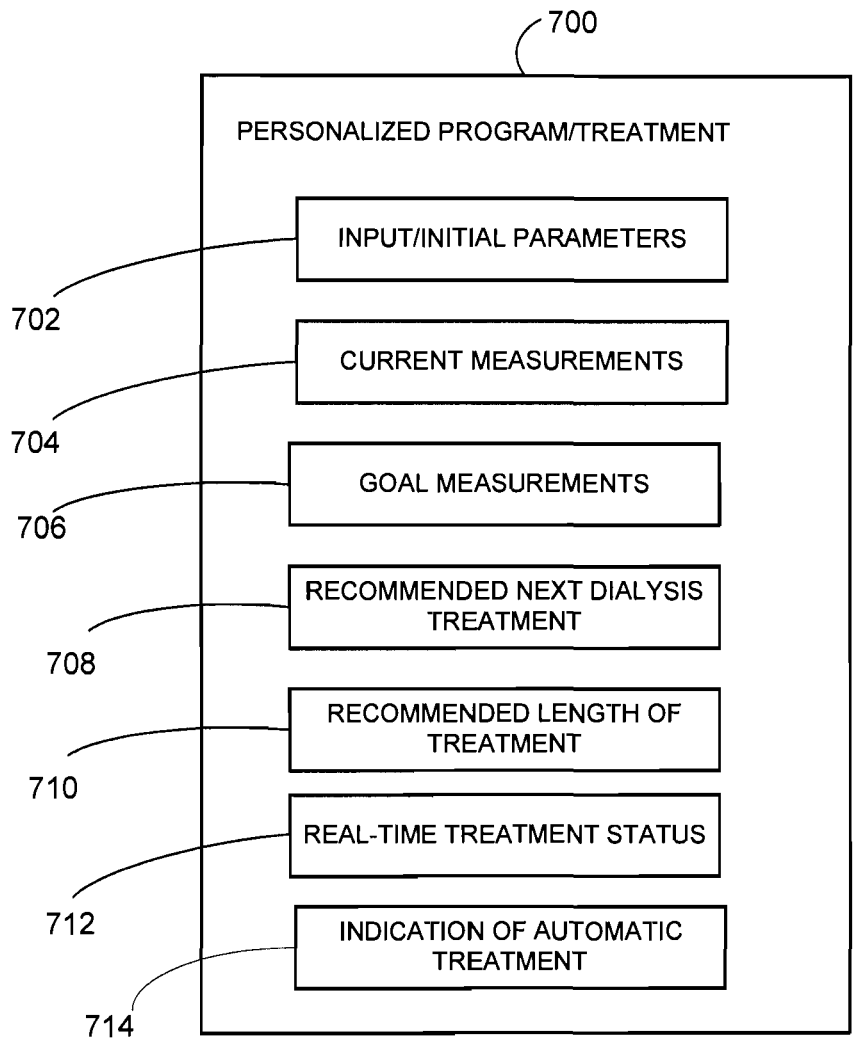
FIG. 7 illustrates a schematic view of a user interface with a renal treatment or data from a medical device, according to some embodiments.

A personalized dialysis display or program may then be generated 310. The personalized program may indicate one or more of a recommended frequency of dialysis treatment or next treatment time 708, recommended length of treatment 710 or a combination thereof (see view 700 of FIG. 7). The personalized program may be a display on the medical device, a printout accessible to a physician or patient, an email, phone call or part of a software program. The software program may be maintained on the Internet or on a local hard drive or server, for example. The report or program may also display input/initial physiological parameters 702, current measurements or status of the patient 704, ideal or healthy measurements or status 706 based on that patient's history and any real-time in-treatment dialysis status 712, if appropriate. An indication of whether the patient is approved for automated treatment is indicated on the report 700. An example of automated treatment is described herein, e.g., with regard to FIGS. 5A and 5B. The report enables the patient to reduce clinic time or increase health status based on receiving the right amount of treatment, for the right amount of time and visits. The amount of testing and over-correction of fluid management may also be reduced. Embodiments of the present invention not only relate to dialysis, but also diuresis, ultrafiltration or any combination of dialysis and filtrations treatments.

The data collected may be utilized by a processor to generate a treatment report or program or may be generated by a physician, for example. As the method and device allow for status monitoring during treatment and away from the clinic, a physician or process may be able to train or adapt the treatment program as it progresses to more closely and accurately monitor the amount of fluid to be removed and the amount of time a patient is in a clinic and undergoing dialysis. Additionally, the method and device allow for spot measurements, long term analysis and remote monitoring of a patient.

Figure 4:
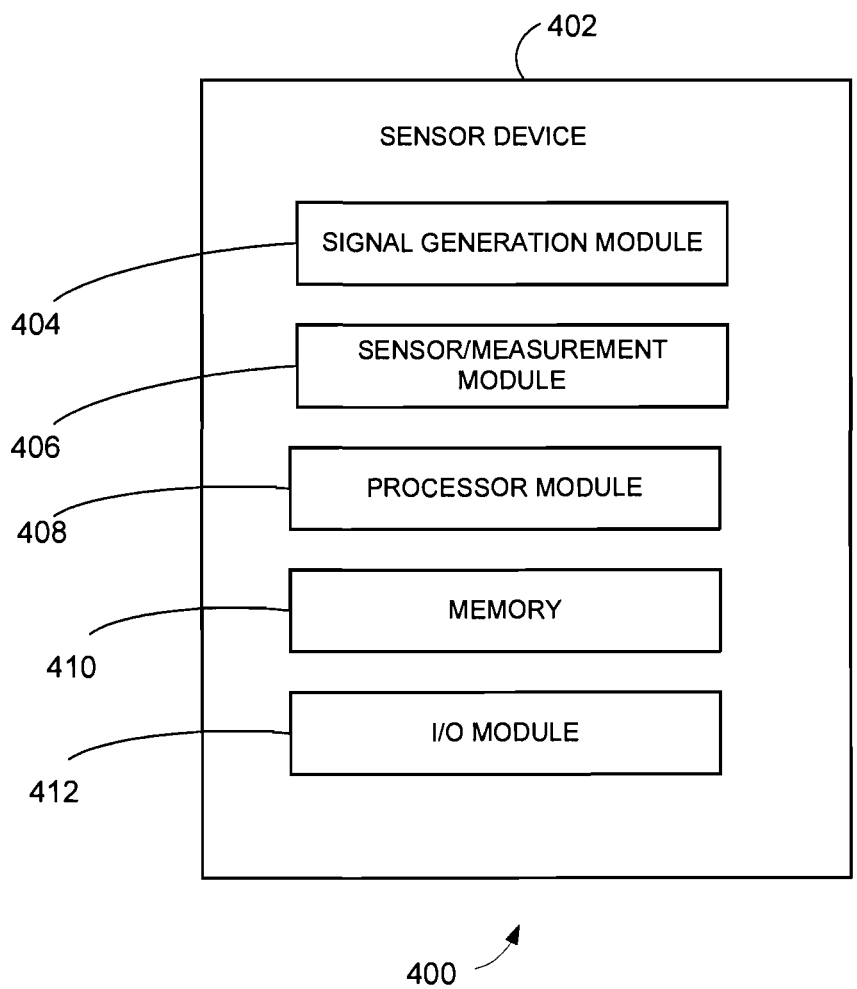
FIG. 4 illustrates a schematic view of a medical device and monitoring system, according to some embodiments.

Referring to FIG. 4, a schematic view 400 of a medical device and monitoring system 402, according to some embodiments. Device 402 can produce a plurality of different signals that can result in changed signals after being applied to the human body to diagnose the renal status of a patient, as variously described herein. Device or system 402 can include a signal generation module 404, a sensor/measurement module 406, a processor module 408, a memory 410, and an input/output module 412. The modules shown may be some combination of hardware, software or integrated hardware and software, for example. The processor module 408 can control operation of the other modules.

Processing module 408 can instruct the signal generation module 404 as to the number of the stimulation pulses and the frequency ranges for each pulse. Processing module 408 can instruct the signal generation module 404 as to the duration of each stimulation signal and the duty cycle of the entire signal used to produce the physiological data. The signal generation module 404 can produce signals at various frequencies and at various amplitudes. The signal generation module 404 produces signals as described herein. In an example, the signal generation module 404 produces a pulsed signal train in which at least one pulse is different than the other pulses, e.g., output at a different frequency than another pulse. The sensor/measurement module 406 can be set by the processor module 408 or be manufactured to sense certain frequencies and amplitudes that are sensed from a patient's body in response to the signals applied by the signal generation module 404. The sensor/measurement module 406 can include various filters to cut off certain low or high end frequencies that are not of interest in producing data that can be used to determine renal status of a patient. The memory 410 stores data sensed by the sensor/measurement module 406 and data representing the signal output by the signal generation module 404. Instructions that can be executed by the processor module 408 can also be stored in the memory 410. The I/O module 412 allows external devices to provide instructions and data to the device 400 and read data from the device 402.

Figure 5A:
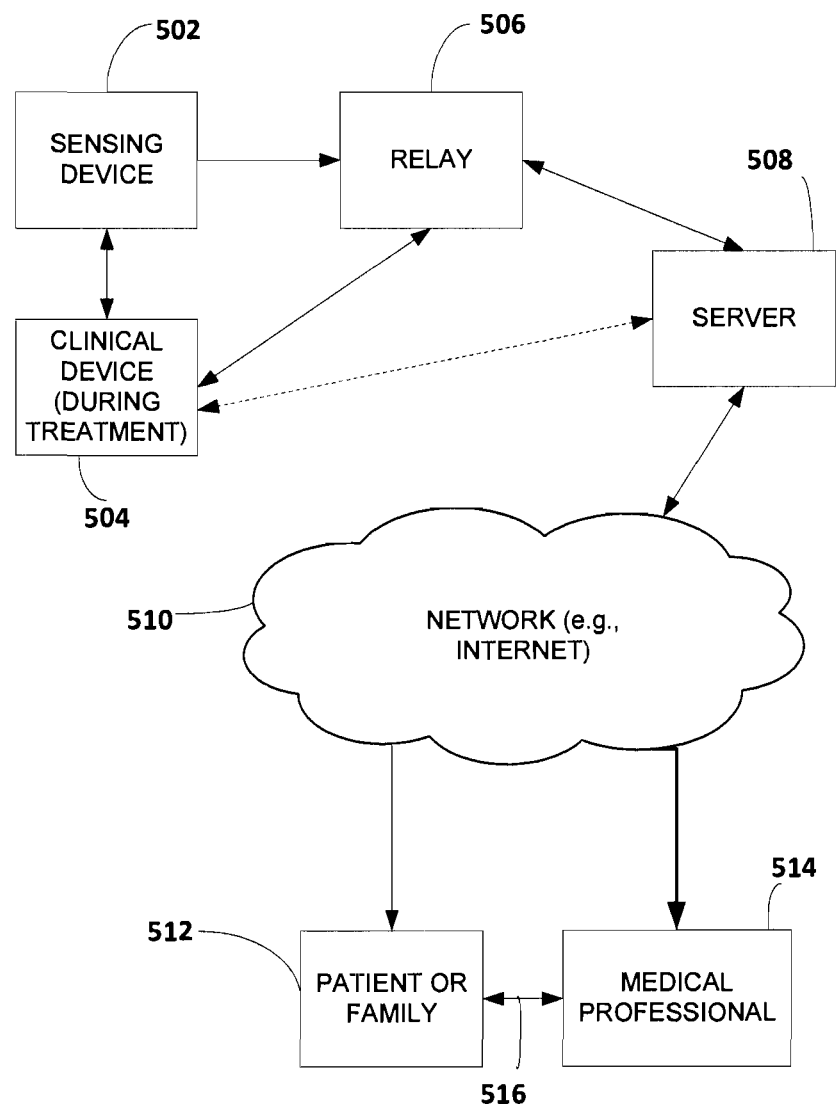
FIG. 5A illustrates a schematic view of a monitoring and reporting system, according to some embodiments.

Referring to FIG. 5A, a schematic view 500 of a monitoring and reporting system, according to some embodiments. A sensing medical device 502 can generate signals which are then relayed 506 to a server 508. The sensing device 502 can include a measuring interface to measure patient data at a measurement site of a patient and one or more electrodes to generate one or more stimulation signals, positioned at the measuring interface and in electrical contact with the measurement site. Sensing device 502 can further include circuitry to measure one or more bioimpedance values, as a result of the generated stimulation signals from the one or more electrodes. Sensing device 502 can include a processor, e.g., logic circuits or programmable processor, to identify one or more physiological parameters, including renal parameters, from the one or more bioimpedance values Alternatively, a clinical device or instrument 504 can generate the signals during a patient treatment, which are then relayed 506 to a server 508. The measurement and analysis of the signals can be performed on-board the device 502 or instrument 504 or performed on the server 508. Alternatively, or in combination, the server 508 can be used to store the analyzed data. The data may be transmitted via a network 510, such as the Internet, an intranet, phone, or other electromagnetic communication system. A patient 512 may receive the data directly or through a medical professional 514. The information may be passed between the patient 512 and professional 514 for example.

When a patient is receiving renal therapy from device 504, various physiological parameters of the patient can be measures. In the example, the sensing device 502 senses fluid levels or fluid conductivity. The clinical device can also measure its blood pump flow, dialysate flow, dialysate conductivity, hematocrit, and other fluid related parameters. In the example where the sensor 502 is an implantable device, it can measure heart rate, heart rate variability, thoracic fluid status, and cardiac stroke volume. Other parameters that can be measured to include in the analysis of renal function and status of the patient include arterial pressure, venous pressure, and blood plasma conductivity. Each of these parameters can be transmitted through relay 506 to the server 508. As a result such parameters can be computed in the server to predict the renal status of the patient in essentially real time or used to output a renal treatment plan for the patient based on data and not on intuition by the medical care provider. The physiological data, the treatment plan and/or current patient status can be fed back to the clinician, physician, or other (patient or family) via the network 510. When the data is computed, it can be used to predict trends in patient data is trended and/or used to determine the effect dialysis or ultrafiltration has on the patient health. For example, the computing of the data can be used to minimize hypotensive episodes for specific patients on an individualized basis.

In a further example, the system 500 can provide essentially real-time hydration, e.g., renal, treatment to a patient using the clinical device 504 while being continuously monitored by the sensor 502. Real-time can mean that the sensor 502 is sensing patient parameters at the same time the clinical device 504 is providing medical treatment to the patient. Real-time can also mean, in an example, that the sensor 502 is sensing patient parameters while the patient is connected to the clinical device 504. In a further example, real-time can be while the patient is in the clinic where the clinical device 504 is located. Simply stated the sensing device 502 is connected to the patient and outputs data relating to the current condition of the patient. The data output by the sensing device can be the raw sensed data, for example, representing essentially real-time data of patient hydration level. The data output by the sensing device 502 can be processed to provide a hydration parameter of the patient and/or statistical data, e.g., trends, of patient hydration. The output data can be determined using bioimpedence of the patient as determined by the sensing device 502, which can apply the systems and methods as described herein. The bioimpedance data measured with sensor device 502, which can be adherent, can provide an accurate indicator of patient hydration level, e.g., patient parameter, in essentially real-time. The sensor device 502 can sense changes in bioimpedance during patient intervention(s), e.g., treatment such as dialysis and diuretics administration. The sensor device 502 senses changes in bioimpedance, which decreases (increases) as a patient becomes more "wet" ("dry"). As a result, the sensor device 502 can apply methods or algorithms that use bioimpedance data to optimally manage in-hospital or in-clinic dialysis or diuresis.

A control system, e.g., server 508, receives the output data from the sensing device 502. The control system applies treatment rules, e.g., stored algorithms and instructions, to the data received from the sensing device 502. The control system can use electronic processors to retrieve the treatment rules from a machine readable memory and apply the rules to the data. The control system can output control instructions to the clinical device to control the operation of the clinical device on the patient. In an example, the clinical device follows the instructions of the control system without intervention of medical personnel, although medical personnel can intervene at either the control system or at the clinical treatment device to override either device if it is in the best interest of the patient.

In particular, the present example the sensor device 502 or the sensor device 502 and control system can provide data representing normalized bioimpedance change that is well correlated with the amount of fluid removed during dialysis, and bioimpedance increases with diuretics administration. As these features make bioimpedance measurements ideal for in-hospital or in-clinic management of dialysis and diuresis.

During hydration therapy, e.g., dialysis, which is an intra-vascular fluid removal process, bioimpedance measurements with sensor device more closely corresponds to interstitial fluid levels. It is not desirable to remove too much fluid during dialysis. However, physiologically, there is a time lag between the level of fluid removal and interstitial fluid level. This is reflected as a delay/lag in the bioimpedance measurements with respect to fluid removal levels. With information regarding this delay, the dialysis can be optimally "paced" (without excess fluid removal) by a physician or a closed-loop system, e.g, server 508 to clinical device 504 using data from sensor device 502. Paced can be the rate at which fluid is removed from the patient. The pace can be at a greater rate to start the therapy and when a threshold is met the rate slows so as to not remove excess fluid. A plurality of benchmarks can be used as thresholds to set the rate of fluid removal. In an embodiment, the delay-parameter can be one determined from a population of patients from a previous study. In another embodiment the delay-parameters can be adaptively computed in real-time for a personalized patient-specific dialysis regimen. The delay parameters can be used in the treatment rules to provide individualized patient treatment, essentially in real-time with a reduced risk of excess fluid removal. This provides many benefits including, but not limited to reduce treatment time and more accurate treatment, which together can result in better patient outcomes and cost savings.

The presently described system can be used with heart failure (HF) patients. In a treatment setting, e.g., hospital, clinic, or other medical treatment facility, diuretics can be administered to HF patients. In a treatment setting, diuretics can be administered several times in a short duration to manage HF symptoms and reduce hydration level in patients with fluid overload. However, such a scheme carries a risk of excessive diuretics administration, which can lead to complications and an undesirable outcome for the patient in both the short term and long term. The present examples use the data from the sensor device 502 to provide bioimpedance measurements that are an accurate and quantitative measure of patient hydration status in comparison to patient symptoms which can be subjective and insufficient. That is the sensor device 502 can provide objective quantitative data with regard to patient hydration. Moreover, the level of bioimpedance change and response lag can be used for the titration of diuretic dosage since the amount of fluid removed is typically a function of diuretic dosage. In particular, measuring the patient's response lag to diuretic administration can avoid excessive diuretic dosages. Here again, the delay can be measured on a population-based level to provide a statistical supported treatment regime. In a further example, the treatment can be based on personalized bioimpedance measurements, e.g., with respect to normalized bioimpedance, for patient-specific management.

As a result, these examples apply to in-treatment center management (hospital, clinic, etc.) of dialysis and diuresis by using a quantitative measure of patient fluid level (e.g., from sensor device 502) along with patient-specific fluid removal response characteristics (data can be stored in sensor device 502, server 508 or part of network 510 or at remote computers). The present examples can provide intelligent methods for personalized medical care.

Figure 5B:
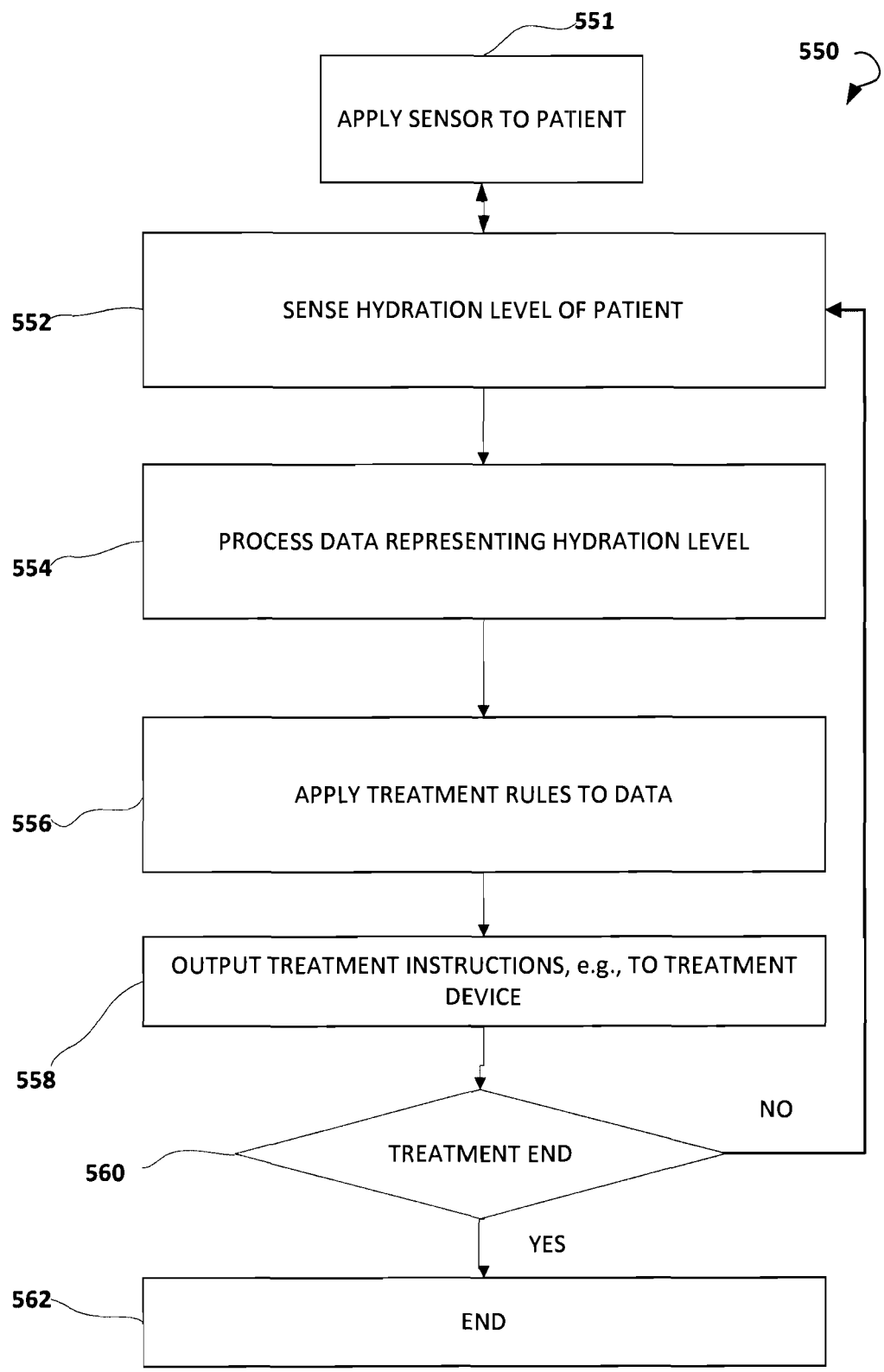
FIG. 5B illustrates a method for patient treatment, according to some embodiments.

Referring to FIG. 5B, a method 550 for patient treatment involving the sensing of hydration levels is shown. At 551, a sensor is applied to the patient. In an example, the sensor is a sensor described herein or a sensor described in patent application no. PCT/US2008/076288 (published as WO 2009/036369), which is hereby incorporated by reference for any purpose. However, in the event of any inconsistencies between the present document and PCT/US2008/076288, the present document controls interpretation. The sensor can include an adherent layer that affixes the sensor to the patient, a sensor (e.g., electrodes) to electromagnetically stimulate or sense patient parameters, a processor or logic unit, a power source, a memory, and a communication device. At 552, hydration level of a patient is sensed, e.g., during treatment of the patient. At 554, the sensed data is processed to provide meaningful data, e.g., representing hydration levels of the patient. The processing of the sensed data can occur on sensor. In an example, the data can be processed by a remote computing device. After processing the data, the data represents hydration levels of the patient. At 556, the hydration data is used with treatment rules to provide treatment instructions. At 558, the treatment instructions are output. The treatment instructions can be sent to the treatment provider or to the physician. The treatment instructions can also be sent to the treatment device. This communication can be made directly without human intervention. As a result, the treatment device can be automatically controlled by the treatment instructions. At 560, a decision is made when treatment is ended. If NO, then the process returns to step 552. If YES, then the method 550 ends at 562. In an example, the treatment instructions output at 558 can include an END or STOP instructions to treatment device.

Figure 6:
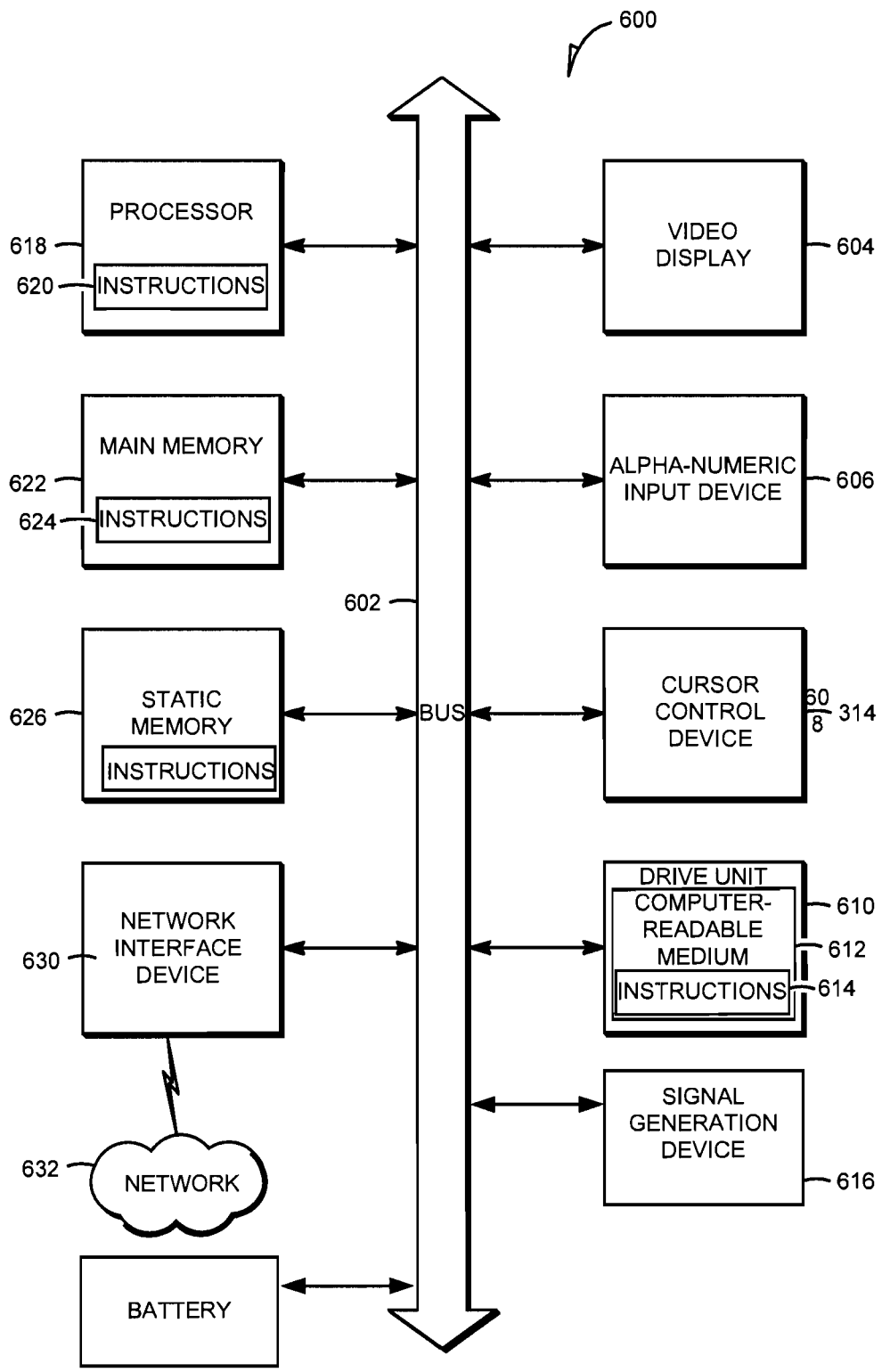
FIG. 6 illustrates a schematic view of medical device and associated system modules, according to some embodiments.

Referring to FIG. 6, a schematic view 600 of medical device and associated system modules, according to some embodiments, is shown. FIG. 6 shows an example of the controller within which a set of instructions are be executed causing the device or system to perform any one or more of the methods, processes, operations, or methodologies discussed herein. In an example, the controller can include the functionality of the computer system.

In an example embodiment, the controller operates as a standalone device or may be connected (e.g., networked) to other controllers. In a networked deployment, the one controller can operate in the capacity of a server (master controller) or a client in server-client network environment, or as a peer machine in a peer-to-peer (or distributed) network environment. Further, while only a single controller is illustrated, the term "controller" shall also be taken to include any collection of devices that individually or jointly execute a set (or multiple sets) of instructions to perform any one or more of the methodologies discussed herein.

The example controller includes a processor 618 (e.g., a central processing unit (CPU) or application specific integrated chip (ASIC)), a main memory 622, and a static memory 626, which communicate with each other via a bus 602. The controller can include a video display unit 604 (e.g., a liquid crystal display (LCD) or a cathode ray tube (CRT)). The controller 618 also includes an alphanumeric input device 604 (e.g., a keyboard), a cursor control device 608 (e.g., a mouse), a storage drive unit 610 (disk drive or solid state drive), a signal generation device 616 (e.g., a speaker), and an interface device 630.

The drive unit 610 includes a machine-readable medium 612 on which is stored one or more sets of instructions (e.g., software 614) embodying any one or more of the methodologies or functions described herein. The software 614 can also reside, completely or at least partially, within the main memory 622 and/or within the processor 618 during execution thereof by the controller, the main memory 622 and the processor 618 also constituting machine-readable media. The software 614 can further be transmitted or received over a network 632 via the network interface device 630.

While the machine-readable medium 614 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by a computer or computing device, e.g., controller, or other machine and that cause the machine to perform any one or more of the methodologies shown in the various embodiments of the present invention. The term "machine-readable medium" shall accordingly be taken to include, but not be limited to, solid-state memories, optical and magnetic media, and carrier wave signals.

Figure 8:
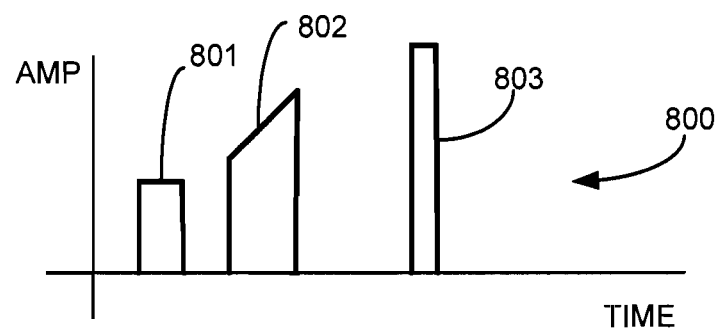
FIG. 8 illustrates a schematic view of signals produces by the devices described herein.

Referring to FIG. 8, a schematic view 800 of a series of signals 801-803 that can be generated by the device 106, 402, 502 or 602. The signals 801, 802, and 803 are each separated from each other in time (x-axis). The signals 801, 802, and 803 each include a frequency component that is not part of the other signals. However, some overlap in frequency can occur. The signals can also include different power or amplitude. These signals are applied to a body of a patient as described herein to produce a signal response that can be sensed by the device(s) 106, 402, 502 or 602.

Figure 9:
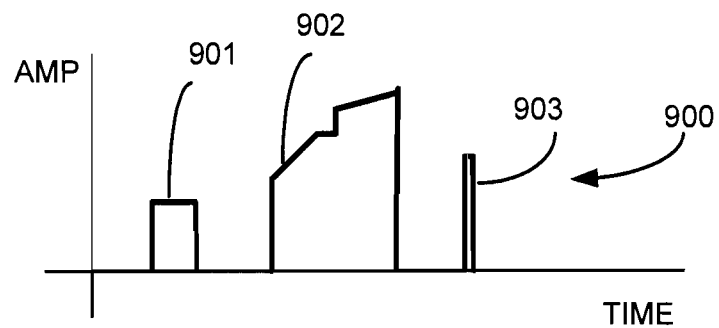
FIG. 9 illustrates a schematic view of signals sensed by the devices described herein.

Referring to FIG. 9, a schematic view 900 of a series of signals 901, 902, and 903 that can be sensed by the device 106, 402 502 or 602 in response to the stimulation signals of FIG. 8. These sensed signals 901, 902, and 903 are the signals that result from the body having the excitation signals applied thereto and the body changing at least one of the excitation signals. The sensed signals 901-903 can be processed using signal processing techniques to produce the renal status of a patient. The renal status can then be used to individualize a renal treatment for that specific patient and not rely on statistical results to predict the most likely treatment plan as is the currently accepted medical treatment for renal diseases.

While the above description shows and described three excitation signals 801-803 and three sensed signals 901-903, it will be recognized that these signals could be divided into further subsets of signals and remain within the scope of the present embodiments. The input signals 801-803 and the sensed signals 901-903 need not be equal in number. For example, a single excitation signal 801, 802 or 803 may result in a plurality of sensed signals and, hence, the number of sensed signals can be more than the number of excitation signals.

An example A of the present description describes methods of monitoring physiological parameters of a patient with renal dysfunction. The method can include electrically connecting one or more medical device electrodes with a measurement site of a patient; generating one or more first stimulation signals, sufficient to provide input physiological parameters specific to the patient; measuring one or more first bioimpedance values from the generated signals; analyzing at least one of the input physiological parameters within the one or more first bioimpedance values; and generating a personalized dialysis program.

An example B can include example A and the input physiological parameters include one or more of a fluid retention value, electrolyte quantity value or hydration level value.

An example C can include example A or B or both, after analyzing at least one of the input physiological parameters, generating second stimulation signals, sufficient to provide one or more second physiological parameters.

An example D can include example A, B or C or any combination thereof and, after generating second stimulation signals, measuring one or more second bioimpedance values from the second generated signals.

An example E can include example A-D, or any combination thereof, after measuring one or more second bioimpedance values, analyzing the at least one of the second physiological parameters within one or more of the second bioimpedance values.

An example F can include example A-E or any combination thereof and the second physiological parameters comprise one or more of a fluid retention value, electrolyte quantity value or hydration level value.

An example G can include example A-F or any combination thereof and a personalized dialysis program indicates one or more the frequency of dialysis treatment, initialization of a dialysis treatment, length of a dialysis treatment, spot analysis of patient health or a combination thereof.

An example H can include example A-G or any combination thereof and dialysis comprises one or more of routine dialysis, diuresis, ultrafiltration or a combination thereof.

An example I can include example A-H or any combination thereof and generating a dialysis program comprises real-time monitoring of changes in one or more of the patients second physiological parameters.

An example J can include example A-I or any combination thereof and generating one or more first stimulation signals comprises generating while the patient is not undergoing treatment and the input physiological parameters are used as a baseline value.

An example K can include example A-J or any combination thereof and generating a dialysis program is generated by a physician, a processor system or a combination thereof.

An example L can include example A-K or any combination thereof and generating one or more first stimulation signals or generating one or more second stimulation signals comprises providing an electrical current between two or more of the one or more electrodes.

An example M can include example A-L or any combination thereof and a medical device to perform any of the methods described in examples A-L.

An example N is a medical device including a measuring interface, located between a device and a measurement site of a patient; one or more electrodes to generate one or more stimulation signals, positioned at the measuring interface and in electrical contact with the measurement site; circuitry to measure one or more bioimpedance values, as a result of the generated stimulation signals from the one or more electrodes; and a processor system to a identify one or more physiological parameters, including renal parameters, from the one or more bioimpedance values.

An example O can include example M-N or any combination thereof and the physiological parameters comprise one or more of a fluid retention value, electrolyte quantity value or hydration level value.

An example P can include example M-O or any combination thereof and the measuring interface comprises a patch.

An example Q can include example M-P or any combination thereof and the circuitry is positioned within the device.

An example R can include example M-Q or any combination thereof and the circuitry is positioned remotely from the device.

An example S can include example M-R or any combination thereof and the processor system is positioned within the device.

An example T can include example M-S or any combination thereof and the processor system is positioned remotely from the device.

An example U can include example M-T or any combination thereof and a display.

An example V can include example M-U or any combination thereof and the processor system being further adapted to analyze the one of more physiological parameters and generated a personalized dialysis program.

An example W can include example M-V or any combination thereof and the device is an implant, a partial implant or an adherent device.

An example X can include any of the above in a closed-loop system providing therapy to a patient based at least on part on sensed data from a patient sensor.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

The invention claimed is:

1. A method of monitoring physiological parameters of a patient with renal dysfunction, comprising:
generating a plurality of first stimulation signals, each of the plurality of first stimulation signals comprising a respective one of a plurality of frequencies and sufficient to measure a respective one of a plurality of first bioimpedance values, wherein the generating of the plurality of first stimulation signals is via one or more electrodes of a medical device, the electrodes are connected with a measurement site of a patient in need of a dialysis program, the measurement site includes a thoracic portion of the patient's skin, and the medical device is an adherent device configured for remote monitoring of the patient;
analyzing each of the measured plurality of first bioimpedance values to identify a personalized baseline of a respective one of a plurality of first physiological parameters, including a plurality of a fluid retention parameter, an electrolyte quantity parameter, or a hydration level parameter;
generating a personalized dialysis program based on the personalized baseline of the plurality of physiological parameters;
generating a plurality of second stimulation signals sufficient to measure a plurality of second bioimpedance values from the plurality of the second generated signals, wherein the plurality of the second stimulation signals is different than the plurality of the first stimulation signals, wherein generating the plurality of second stimulation signals comprises generating the plurality of second stimulation signals during dialysis according to the personalized dialysis program;
analyzing each of the measured plurality of second bioimpedance values to identify a respective one of a plurality of second physiological parameters; and
adjusting the personalized dialysis program based on a comparison of the first physiological parameters with the second physiological parameters.

2. The method of claim 1, wherein the generating of the first stimulation signals and the analyzing of the first bioimpedance values is performed over a period of a week or more.

3. The method of claim 1, wherein the plurality of second physiological parameters comprise a plurality of a fluid retention value, electrolyte quantity value or hydration level value.

4. The method of claim 1, wherein the personalized dialysis program indicates one or more of a frequency of dialysis treatment, initialization of a dialysis treatment, length of a dialysis treatment, or spot analysis of patient health.

5. The method of claim 1, wherein dialysis comprises one or more of routine dialysis, diuresis, or ultrafiltration.

6. The method of claim 1, wherein generating the plurality of the first stimulation signals comprises generating while the patient is not undergoing treatment.

7. The method of claim 1, wherein generating the plurality of the first stimulation signals and generating the plurality of the second stimulation signals comprises providing an electrical current between two or more of the one or more electrodes.

8. The method of claim 1, wherein each of the plurality of different frequencies corresponds to the one or more fluid retention, electrolyte quantity or hydration level values determined using the measured bioimpedance values.

9. The method of claim 1, further including generating the plurality of second stimulation signals at times subsequent to the plurality of generated first stimulation signals to establish at least one of a fluid retention profile or a dialysis profile based on one or more second physiological parameters.

10. The method of claim 9, wherein the adjusted personalized dialysis program provides one or more of a recommended next dialysis treatment or recommended length of next dialysis treatment.

11. The method of claim 1, wherein generating the plurality of the first stimulation signals and the plurality of second stimulation signals includes generating the stimulation signals at a plurality of different amplitudes.

12. A method of monitoring physiological parameters of a patient with renal dysfunction, comprising:
generating one or more first stimulation signals sufficient to measure one or more first bioimpedance values from the generated signals, wherein the generating of the one or more first stimulation signals is via one or more electrodes of a medical device, the electrodes are connected with a measurement site of a patient in need of a dialysis program, the measurement site includes a thoracic portion of the patient's skin, and the medical device is an adherent device configured for remote monitoring of the patient;
analyzing the measured one or more first bioimpedance values to identify a personalized baseline of one or more physiological parameters, including renal parameters;
generating a personalized dialysis program based on the analysis;
generating one or more second stimulation signals sufficient to measure one or more second bioimpedance values from the one or more generated second stimulation signals, wherein the one or more second stimulation signals are generated subsequent to the one or more first stimulation signals and are different than the one or more first stimulation signals, wherein the generating of the one or more second stimulation signals comprises generating the one or more second stimulation signals during dialysis according to the personalized dialysis program, the method further comprising;

analyzing the measured one or more second bioimpedance values to identify one or more second physiological parameters for comparison to the one or more first physiological parameters; and adjusting the personalized dialysis program based on the comparison of the personalized baseline of the one or more physiological parameters with the one or more second physiological parameters.

* * * * *